United States Patent [19]

Thwaites et al.

[11] Patent Number: 5,372,127
[45] Date of Patent: Dec. 13, 1994

[54] SUMP FOR AN ANAESTHETIC VAPORISER

[75] Inventors: David J. Thwaites, Ilkley; David C. Sampson, Cowling, both of Great Britain

[73] Assignee: The BOC Group plc, Surrey, England

[21] Appl. No.: 39,026

[22] PCT Filed: Sep. 18, 1991

[86] PCT No.: PCT/GB91/01591
§ 371 Date: Mar. 25, 1993
§ 102(e) Date: Mar. 25, 1993

[87] PCT Pub. No.: WO92/04930
PCT Pub. Date: Apr. 2, 1992

[30] Foreign Application Priority Data

Sep. 26, 1990 [GB] United Kingdom .............. 9020881.0
Apr. 26, 1991 [GB] United Kingdom .............. 9109025.8

[51] Int. Cl.$^5$ ...................... A61M 11/00; A61M 16/00
[52] U.S. Cl. ...................... 128/203.12; 128/203.13; 128/204.14; 128/204.17; 128/200.11; 128/203.26; 128/203.27
[58] Field of Search ............. 424/40; 128/203.13, 128/203.12, 204.14, 204.17, 200.11, 200.24, 203.26, 203.27; 261/65

[56] References Cited

U.S. PATENT DOCUMENTS

| | | | |
|---|---|---|---|
| 3,219,795 | 3/1962 | Wiseman | 392/402 |
| 3,319,046 | 5/1967 | Katzman | 392/337 |
| 4,607,634 | 8/1986 | Clapham | 128/204.14 |

FOREIGN PATENT DOCUMENTS

| | | |
|---|---|---|
| 0263049 | 4/1988 | European Pat. Off. . |
| 2097272 | 11/1982 | United Kingdom . |
| 2109098 | 5/1983 | United Kingdom . |
| 2150676 | 7/1985 | United Kingdom . |
| 2190989 | 12/1987 | United Kingdom . |
| 2227821 | 8/1990 | United Kingdom . |

Primary Examiner—Thurman K. Page
Assistant Examiner—Raj Bawa
Attorney, Agent, or Firm—Roger N. Rathbun; Larry R. Cassett

[57] ABSTRACT

A sump for an anaesthetic vaporiser comprises a vaporising chamber for liquid anaesthetic agent, a heater for liquid anaesthetic agent contained within the chamber, and a partition member of which at least a portion extends into the chamber to entrap a portion of liquid anaesthetic agent at a location in close proximity to the heater, the member having a partition outlet for anaesthetic agent vapor through the partition member at a position above the maximum level of anaesthetic agent within the partition member. The partition member allows a portion only of liquid anaesthetic agent within the vaporizing chamber to be heated, so that the temperature required of the liquid agent for operation of the vaporiser can be reached rapidly. The sump finds particular application in connection with the use of low boiling point anaesthetic agents such as 2-(difluoromethoxy)-1,1,1,2-tetrafluoroethane.

5 Claims, 1 Drawing Sheet

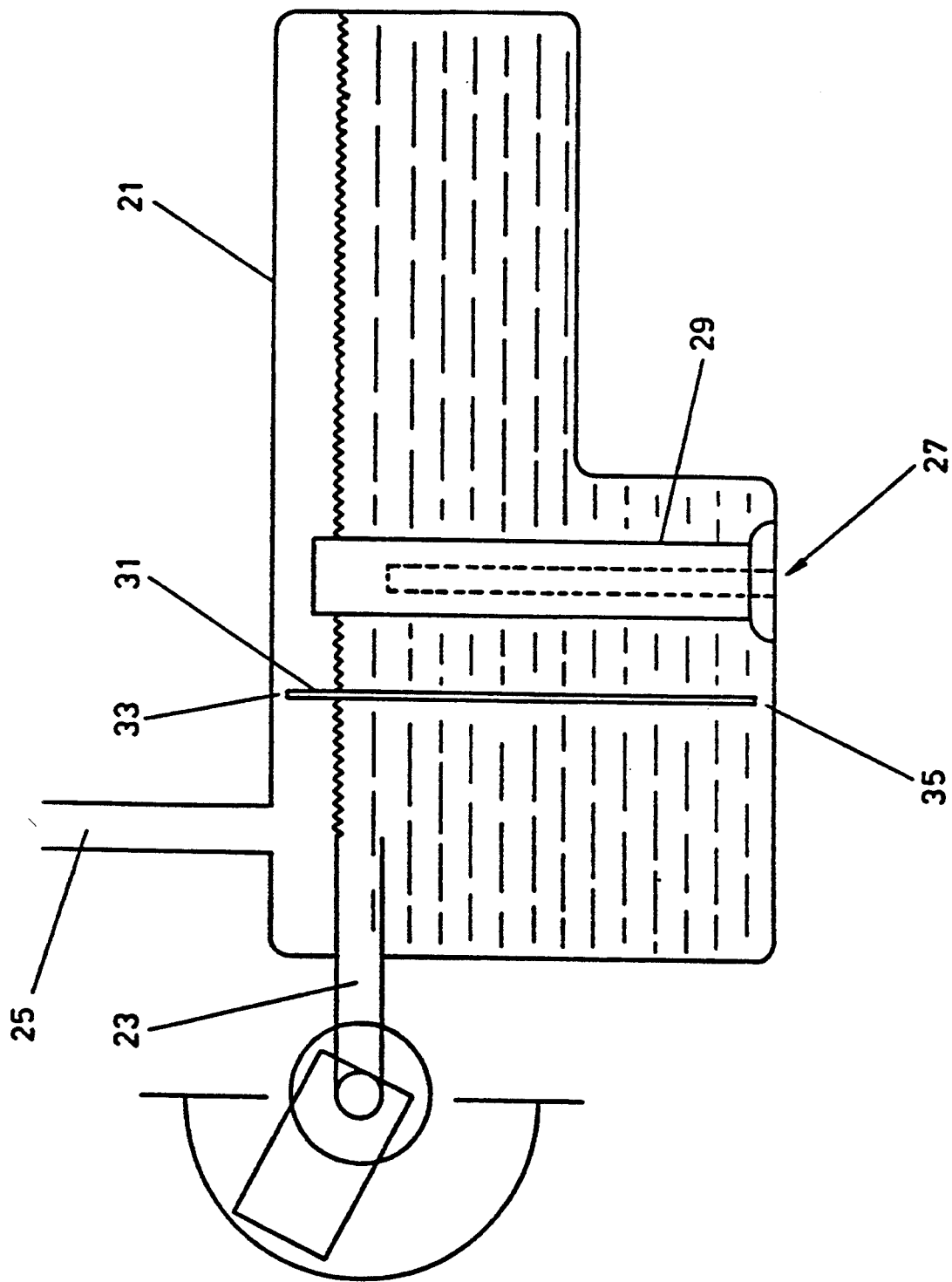

SUMP FOR AN ANAESTHETIC VAPORISER

This invention relates to a sump for an anaesthetic agent vaporiser, and to a method of vaporising an anaesthetic agent. A known vaporiser for volatile anaesthetic agents Includes a vaporising chamber for liquid anaesthetic agent, and an inlet into the vaporising chamber for a carrier gas which entrains anaesthetic agent vapor within the chamber above the surface of the liquid anaesthetic agent and carries the vapor out of the vaporiser for adminstration to a patient. Such a vaporiser is disclosed in GB-1224478.

The vapor pressure of many volatile anaesthetic agents is heavily dependent on the ambient temperature at which the vaporiser operates. In order to minimise the dependence of vapour pressure on the ambient temperature in which the vaporiser operates, it is known to provide a heater within the vaporising chamber by which the temperature of anaesthetic agent within the chamber can be controlled. It is to be understood however that the temperature of the anaesthetic agent is maintained significantly below its boiling point; anaesthetic agent vapour is therefore carried out of the vaporising chamber not under its own vapour pressure, but entrained in the carrier gas which is supplied to the chamber.

A recently introduced anaesthetic agent, 2-(difluoromethoxy)-1,1,1,2-tetrafluoroethane has a relatively low boiling point in the region of ambient temperature. Conventional techniques for administration of anaesthetic agents having boiling points well above ambient temperature, using vaporisers such as that disclosed in GB-1224478, are not generally applicable to this new agent. Recently developed vaporisers for low boiling point anaesthetic agents are disclosed in EP-A-438218 and European patent application no. 91306823.5. Subject matter disclosed In those documents is incorporated in this specification by these references to the documents. A vaporiser includes a vaporising chamber for liquid anaesthetic agent, in which the agent is vaporised. The vaporiser further includes a passage which extends from an inlet for carrier gas to an outlet. Anaesthetic agent vapour from the vaporising chamber flows from the chamber under the pressure which is generated as a result of the liquid agent having been heated to cause it to boil, to mix with carrier gas in the passage so that the carrier gas which is discharged from the outlet, for administration to a patient, is a mixture of carrier gas and anaesthetic: agent vapour.

SUMMARY OF THE INVENTION

In vaporisers for low boiling point vaporisers, it is particularly important that the temperature of the liquid anaesthetic agent within the vaporising chamber be controlled carefully, because the pressure of the anaesthetic agent vapour is so heavily dependent on the temperature of the liquid anaesthetic agent relative to its boiling point. It can also be desired in many instances to reach the controlled temperature of the liquid anaesthetic agent as quickly as possible after replenishing the supply of agent to the vaporising chamber or after first turning on the vaporiser.

The present invention provides a sump for an anaesthetic vaporiser, which includes a partition member located in the vaporising chamber by which a portion of the liquid anaesthetic agent can be entrapped, for heating by means of an associated heater.

Accordingly, the invention provides a sump for an anaesthetic agent vaporiser, which comprises:
(a) a vaporising chamber for liquid anaesthetic agent,
(b) a heater for liquid anaesthetic agent container within the chamber, and
(c) a partition member in the form of a plate which extends across the vaporising chamber and cooperates with the internal wall of the vaporising chamber to entrap a portion of liquid anaesthetic agent at a location immediately adjacent the heater, the plate having a partition outlet at a position above the maximum level of liquid anaesthetic agent within the space defined by the partition member and the internal wall of the vaporising chamber, through which anaesthetic agent vapour can pass through the plate.

The sump of the invention has the advantage that a quantity of liquid anaesthetic agent can be heated rapidly to a desired temperature, which is above the boiling point of the anaesthetic agent, so that a pressure of anaesthetic agent vapour can be established to enable the vapour to flow from the vaporising chamber for administration to a patient. The provision of a partition member, by which a portion of the liquid anaesthetic agent in the vaporising chamber can be entrapped, allows the desired temperature in the liquid anaesthetic agent to be reached without having to heat all of the liquid in the vaporising chamber. The significance of this advantage can be appreciated in the context of refilling of the vaporising chamber of a sump, when existing liquid anaesthetic agent which has been heated to cause vaporisation of the agent is supplemented by additional liquid agent which has not been so heated. The resulting reduction in the temperature of the liquid agent in the vaporising chamber will lead to an immediate reduction in the pressure of the anaesthetic agent vapour. This can have significant adverse consequences if prolonged and if the refilling takes place while anaesthetic agent is being administered from the vaporiser to a patient. The sump of the present invention allows the pressure of the anaesthetic agent vapour to be restored to a desired level quickly after such a refilling operation, so that any reduction in the supply of anaesthetic agent to a patient under anaesthesia is minimised. It must further be appreciated that the likelihood of refilling of the vaporising chamber of a vaporiser, while agent is being administered to a patient, is somewhat greater in the case of 2-(difluoromethoxy)-1,1,1,2-tetrafluoroethane and other low boiling point anaesthetic agents than in the case of conventional agents because of the greater volumes of that agent which are administered during anaesthesia.

In another aspect, the invention provides a method of vaporising an anaesthetic agent, comprising providing a sump for an anaesthetic agent vaporiser which comprises:
(a) a vaporising chamber for liquid anaesthetic agent,
(b) a heater for liquid anaesthetic agent contained within the chamber, and
(c) a partition member in the form of a plate which extends across the vaporising chamber and cooperates with the internal wall of the vaporising chamber to entrap a portion of liquid anaesthetic agent at a location immediately adjacent the heater, the plate having a partition outlet at a position above the maximum level of liquid anaesthetic agent within the space defined by the partition member and the internal wall of the vaporising chamber, through which anaesthetic agent vapour can pass through the plate;
supplying heat to liquid anaesthetic agent entrapped within the said space by means of the heater to cause the anaesthetic agent to boil; and allowing anaesthetic agent vapour to flow from within the space defined by the partition member four supply to a patient, under the pressure of the anaesthetic agent vapour generated as a result of the heat supplied to the liquid anaesthetic agent from the heater.

The sump of the invention may be arranged so that anaesthetic agent vapour is discharged through the partition outlet into the portion of the vaporising chamber outside the partition member, the vaporising chamber including a chamber outlet for anaesthetic agent vapour from the sump. This arrangement has the advantage that carry over of liquid anaesthetic agent from the vaporising chamber with anaesthetic agent vapour can be minimised, by arranging for the flow of vapour from within the space defined by the partition member out of the sump to be along a tortuous path, allowing liquid agent associated with anaesthetic agent vapour, for example as a result of agitation on boiling of the liquid, to drop back into the vaporising chamber. For example, the chamber outlet and the partition outlet may be offset from one another so that the two outlets do not overlap with one another. The possibility of minimising liquid carry over has the advantage that the quantity of anaesthetic agent supplied to a patient can be controlled more accurately, since the agent which is being supplied is more likely to be in vapour form which can be quantified, and less likely to include liquid which might vaporise between the vaporising chamber and the patient, or within the patient's breathing circuit, increasing significantly the effective quantity of anaesthetic agent vapour which is received by the patient.

When the partition member and the vaporising chamber each have outlets, the path which is followed by anaesthetic agent vapour passing through those outlets may be arranged to be tortuous by arranging the outlets so that vapour flowing through each of the outlets follows respective paths which are non-parallel. For example, one of the outlets may be in a vertical member, and the other of the outlets may be in a horizontal member. In this event, it will be understood that the two outlets will be such that they are offset from one another and do not overlap. When the outlets are in members which are not perpendicular to one another, they are to be considered to be offset from one another and not to overlap when the projection of one of the outlets onto the other outlet does not overlap with that other outlet.

The partition member is as a plate which extends across the vaporising chamber and cooperates with the internal wall of the vaporising chamber to define a space within the chamber for liquid anaesthetic agent to be heated by the heater. The plate may extend for example across the vaporising chamber or around a corner thereof. The plate includes at least one opening in it located above the maximum level of the liquid anaesthetic agent in the vaporising chamber, through which anaesthetic vapour can pass from within the space defined by the partition member, and it may include one or more openings located below the level of the liquid agent in the vaporising chamber, through which liquid agent can pass from outside the partition member, to replace that which has been lost by vaporisation, and so to maintain the levels of liquid agent inside and outside the partition member approximately equal.

It can be preferred particularly that the heater has the form of an elongate member.

BRIEF DESCRIPTION OF THE DRAWINGS

Embodiments of the invention will now be described by way of example, with reference to the accompanying drawings, which is a schematic representation of an embodiment of sump for an anaesthetic vaporiser.

DESCRIPTION OF THE PREFERRED

Referring to the drawing, which shows a sump for an anaesthetic vaporiser which includes a vaporising chamber 21, having an inlet 23 for liquid anaesthetic agent and an outlet 25 for anaesthetic vapour. A cylindrical heater 27 is located within a cylindrical finger 29 for heating liquid anaesthetic agent contained within the vaporising chamber to a temperature which is greater than the boiling point of the agent.

A plate 31 is provided between the heater and its associated finger and the outlet 25 from the vaporising chamber. As shown, the plate extends across the chamber and cooperates with the internal wall of the vaporising chamber to define a space within the chamber for liquid anaesthetic agent which is to be heated by the heater. The plate has openings 33 extending through it at its upper end to allow the passage of anaesthetic vapour from within it towards the outlet 25 from the vaporising chamber. The plate also has openings 35 extending through it at its lower end through which liquid anaesthetic agent can pass into the space of the vaporising chamber defined by the plate and the internal wall of the chamber to replace the agent which is lost from that space by vaporisation.

The plate controls movement of the liquid anaesthetic agent within it as a result of the application to it of heat which can cause it to become agitated as it boils, so as to minimise the carriage of liquid agent into the outlet 25 from the chamber together with anaesthetic vapour.

We claim:

1. A sump for an anaesthetic agent vaporiser, which comprises:
   (a) a vaporising chamber for liquid anaesthetic agent,
   (b) a heater for liquid anaesthetic agent contained within the chamber, and
   (c) a partition member in the form of a plate which extends across the vaporising chamber and cooperates with the internal wall of the vaporising chamber to entrap a portion of liquid anaesthetic agent at a location in close proximity to the heater, the plate having a partition outlet at a position above the maximum level of liquid anaesthetic agent within the space defined by the partition member and the internal wall of the vaporising chamber, through which anaesthetic agent vapour can pass through the plate.

2. A sump as claimed in claim 1, in which the partition outlet discharges the anaesthetic agent vapour into the vaporising chamber, and in which the vaporising chamber includes a chamber outlet for anaesthetic agent vapour.

3. A sump as claimed in claim 2, in which the chamber outlet and the partition outlet are offset from one another so that the two outlets do not overlap with one another and so that the path followed by anaesthetic agent vapour leaving the sump through the partition and chamber outlets is tortuous.

4. A sump as claimed in claim 2, in which the heater has the form of an elongate member.

5. A method of vaporising an anaesthetic agent, comprising providing a sump for an anaesthetic agent vaporiser which comprises:
   (a) a vaporising chamber for liquid anaesthetic agent,
   (b) a heater for liquid anaesthetic agent contained within the chamber, and
   (c) a partition member in the form of a plate which extends across the vaporising chamber and cooperates with the internal wall of the vaporising chamber to entrap a portion of liquid anaesthetic agent at a location in close proximity to the heater, the plate having a partition outlet at a position above the maximum level of liquid anaesthetic agent within the space defined by the partition member and the internal wall of the vaporising chamber, through which anaesthetic agent vapour can pass through the plate;

supplying heat to liquid anaesthetic agent entrapped within the said space by means of the heater to cause the anaesthetic agent to boil; and allowing anaesthetic agent vapour to flow from within the space defined by the partition member for supply to a patient, under the pressure of the anaesthetic agent vapour generated as a result of the heat supplied to the liquid anaesthetic agent from the heater.

* * * * *